United States Patent
Mathieu et al.

(10) Patent No.: US 6,500,993 B1
(45) Date of Patent: *Dec. 31, 2002

(54) PROCESS FOR PREPARING HALOGENATED HYDROCARBONS

(75) Inventors: Véronique Mathieu, Wavre (BE); Jean-Paul Schoebrechts, Grez-Doiceau (BE)

(73) Assignee: Solvay (Societe Anonyme) (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/433,506

(22) Filed: Nov. 3, 1999

(30) Foreign Application Priority Data

Nov. 5, 1998 (BE) .............................................. 9800807

(51) Int. Cl.$^7$ .......................... C07C 19/08; C07C 17/26
(52) U.S. Cl. ....................................... 570/127; 570/257
(58) Field of Search ................................. 570/127, 257

(56) References Cited

U.S. PATENT DOCUMENTS

| | | | |
|---|---|---|---|
| 3,268,603 A | 8/1966 | Scherling | 570/257 |
| 3,454,657 A | 7/1969 | Decker et al. | 260/651 |
| 3,649,698 A | 3/1972 | Goble et al. | 570/257 |
| 3,651,019 A | 3/1972 | Asscher et al. | |
| 3,862,978 A | 1/1975 | Decker et al. | |
| 5,446,217 A | 8/1995 | Van Der Puy et al. | |
| 5,792,893 A | 8/1998 | Wilson et al. | |
| 5,917,098 A | 6/1999 | Bertocchio et al. | |

FOREIGN PATENT DOCUMENTS

| | | |
|---|---|---|
| EP | 0 729 932 | 4/1996 |
| EP | 0 787 707 | 8/1997 |
| FR | 1288511 | 5/1961 |
| GB | 1146463 | 3/1969 |
| GB | 2 188 929 | 10/1987 |
| WO | 95/04021 | 2/1995 |
| WO | 95/04022 | 2/1995 |
| WO | 96-101797 | 1/1996 |
| WO | 97/05089 | 2/1997 |
| WO | 97/07083 | 2/1997 |
| WO | 97/15540 | 5/1997 |
| WO | 98/50329 | 11/1998 |
| WO | 98/50330 | 11/1998 |
| WO | 99/07659 | 2/1999 |
| ZA | 98/3775 | 1/2000 |
| ZA | 98/3781 | 1/2000 |

OTHER PUBLICATIONS

Kotora et al., "Addition of Tetrachloromethane to Halogenated Ethenes Catalyzed by Transition Metal Complexes," *Journal of Meolecular Catalysts*, 77:51–60 (1992).

Ullmann's Encyclopedia of Industrial Chemistry, 1992, vol. B4, p. 387–388.

Asscher and Vofsi, *Chlorine Activation by Redox Transfer. Part II. The addition of Carbon Tetrachloride to Olefins*, 1963, p. 1887–1896.

T. Asahara et al., "Telomerization of Binylchloride with Carbon Tetrachloride Initiated by n-butylamine and Metallic Salts", Kogyo Kagaku Zasshi, 72 pp. 1526–1529 (1969).

R. Freidlinda et al., "Telomerization of 2-Chloropropene with Carbon Tetrachloride", Bull. Acad. Sci. USSR, 28, pp. 1766–1769 (1979).

Belbachir et al., "Reaction avec le tetrachlorure de carbone par catalyse redox", Makromol. Chem 185 pp. 1583–1595 (1984).

Kotora et al., "Selective Additions of Polyhalogenate Compounds to Chloro Substituted Ethenes Catalyzed by a Copper Complex", React. Kinet. Catal, Lett. 44, No. 2, pp. 415–419 (1991).

Primary Examiner—Sreeni Padmanabhan
Assistant Examiner—Sikarl A. Witherspoon
(74) *Attorney, Agent, or Firm*—Connolly Bove Lodge & Hutz LLP

(57) ABSTRACT

Process for preparing halogenated hydrocarbons, comprising at least 3 carbon atoms, by catalytic telomerization between a haloalkane and an olefin in the presence of an amine with a high boiling point as co-catalyst. 1,1,1,3,3-Pentachloropropane and 1,1,1,3,3-pentachlorobutane are thus prepared under mild conditions in good yield and the catalyst/co-catalyst system can be easily separated by distillation and recycled.

17 Claims, No Drawings

PROCESS FOR PREPARING HALOGENATED HYDROCARBONS

The present invention relates to a process for preparing halogenated hydrocarbons, comprising at least 3 carbon atoms, by catalytic reaction between a haloalkane and a olefin, in particular a halogenated olefin.

The addition of a haloalkane to an olefin is a well-known reaction, generally referred to as a telomerization reaction. Very often, copper derivatives are used to catalyse this addition reaction. For example, patent U.S. Pat. No. 3,651,019 describes the addition of carbon tetrachloride to olefins in the presence of catalysts containing copper or iron. That patent describes reactions in batches (non-continuous process) and, at the end of the reaction, the catalyst is not recovered. This makes the process economically unattractive. In the event of separation of the constituents of the reaction mixture by distillation, the catalyst would precipitate in the boiling vessel of the distillation column, thereby making its recycling difficult.

Patent application WO 97/07083 describes a process for preparing halogenated hydrocarbons by telomerization, preferably under the catalytic action of cuprous chloride in the presence of t-butylamine as co-catalyst, in which the mixture of products derived from the reaction step is separated in several steps. The mixture is first separated by a flash distillation into a first flow containing the unconverted reagents and the co-catalyst, and into a second flow comprising the halogenated hydrocarbon and the catalyst. The catalyst is then separated from this second flow by filtration, after which the halogenated hydrocarbon is purified by distillation. This process requires a filtration of the catalyst in solid form, which is always a difficult step to control in an industrial plant, in particular in a continuous synthetic process.

Patent application WO 97/05089 describes another process for preparing halogenated hydrocarbons by telomerization, under the catalytic action of a copper catalyst dissolved in a solvent which is immiscible with the desired halogenated hydrocarbon, thus making it possible to separate the catalyst/solvent system from the halogenated hydrocarbon by decantation. However, the production efficiency of this process remains very low.

A need consequently exists to provide a telomerization process which makes it possible to prepare halogenated hydrocarbons in excellent yield and excellent production efficiency, while at the same time also making it possible to recover the catalyst easily and return it to the reactor in a simple manner.

The present invention relates to a process for preparing a halogenated hydrocarbon, comprising the following steps:
(a) a reaction step between a haloalkane and an olefin in the presence of a catalyst and a co-catalyst under conditions which are suitable for producing the halogenated hydrocarbon, the co-catalyst being chosen from amines which are less volatile than the halogenated hydrocarbon;
(b) a separation step of the mixture of reaction products from step (a) wherein at least a first fraction comprising the halogenated hydrocarbon and a second fraction comprising the catalyst and the co-catalyst are obtained;
(c) optionally a recycling step of at least a part of the second fraction into step (a).

By "fraction" we relate to any part of the mixture enriched in certain of its constituents, obtained either in continous flow or in a discontinuous treatment. By "recycling" we relate to any operation of recovery and reuse indifferently in a continous or in a discontinuous mode.

In a specific mode of carrying out of the invention, in step (b) the mixture of reaction products from step, (a) is subjected to a separation by distillation, and, in addition to the first fraction comprising the halogenated hydrocarbon and the second fraction comprising the catalyst and the co-catalyst a third fraction comprising reagents not consumed is obtained, and in a step (c) also at least a part of the third fraction is recycled optionally to step (a).

The use, as co-catalyst, of an amine whose boiling point is higher than that of the halogenated hydrocarbon makes it possible to separate the halogenated hydrocarbon from the reagents not consumed and the catalyst/co-catalyst active complex by distillation. Since the catalyst remains soluble in the amine after the removal of the reagents not consumed and the halogenated hydrocarbon, it can thus be recovered easily.

In the reaction step (a) of the process according to the present invention, a haloalkane and a olefin, preferably a halogenated olefin are reacted in the presence of a catalyst and a co-catalyst to form a halogenated hydrocarbon, the co-catalyst being chosen from amines which are less volatile than the halogenated hydrocarbon produced.

Amines comprising from 8 to 25 carbon atoms, in particular aliphatic amines, may be suitable as co-catalysts in the process according to the invention. Aliphatic amines comprising from 10 to 22 carbon atoms are preferred. Very special preference is given to amines whose alkyl chain is branched, and more especially to tert-alkyl amines corresponding to the general formula (I)

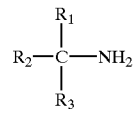

in which $R_1$, $R_2$ and $R_3$ represent C1–C8 alkyl groups. As non-limiting examples of amines with a high boiling point, in particular which are less volatile than 1,1,1,3,3pentachloropropane and 1,1,1,3,3pentachloro butane, mention may be made in particular of nonylamine, decylamine, undecylamine, dodecylamine and collidines. Amines corresponding to formula (I) are, in particular, the tert-alkyl amines Primene® 81-R and JM-T sold by Rohm & Haas Company. These latter amines are preferred. Mixtures of amines can also be used in the present process. The amines used as co-catalysts in the process according to the invention have also been found to be markedly more stable in the presence of the catalyst and the haloalkane than the amines used in the prior processes, such as isopropylamine and t-butylamine.

The haloalkanes used in the process according to the present invention are generally saturated organic compounds. They preferably contain from one to three carbon atoms and preferably at least 2 chlorine atoms. They can also comprise other substituents, such as other halogen atoms, alkyl groups or haloalkyl groups. As examples of haloalkanes according to the present invention, mention may be made of dichloromethane, chloroform, carbon tetrachloride, 1,1,1-trichloroethane or 1,1,2-trichloro-1,2,2-trifluoroethane. Carbon tetrachloride is most particularly preferred.

The olefins used in the process according to the present invention are, for example, linear or branched olefins comprising from 2 to 10 carbon atoms which may themselves be optionally substituted. They can be substituted, for example, with halogen atoms, alkyl or haloalkyl groups, nitrile (CN) groups or carboxylic acid (COOH) groups. Specific examples of such olefin are, amongst others, ethylene, propylene, butylene and the 1-olefines comprising from 2 to 10 carbon atoms. The olefin is preferably a halogenated olefin. The halogenated olefins are preferably derivatives of a haloethene or of a halopropene, which may themselves be optionally substituted. The halogenated olefins used in the process according to the present invention preferably correspond to the formula

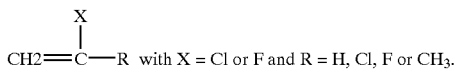

$CH_2=C-R$ with $X = Cl$ or $F$ and $R = H$, $Cl$, $F$ or $CH_3$.

Preferably, the halogenated olefin is a chlorinated olefin. As non-limiting examples of halogenated olefins, mention may be made of vinyl chloride, vinylidene chloride, trichloroethylene and the various chloropropene isomers, such as 1-chloro-1-propene, 2-chloro-1-propene and 3-chloro-1-propene. Among these compounds, those in which X=Cl and R=H or $CH_3$ are preferred. Vinyl chloride and 2-chloro-1-propene are particularly suitable.

The halogenated hydrocarbons obtained according to the process of the present invention generally belong to the family of chlorinated hydrocarbons comprising from 3 to 12 carbon atoms. Often they belong to the family of chloropropanes, chlorobutanes or chloropentanes. The carbon atoms in the said chloropropanes, chlorobutanes and chloropentanes can also be substituted with other functional groups, such as other halogen atoms (for instance fluorine, bromine or iodine atoms), alkyl or haloalkyl groups, nitrile (CN) groups or carboxylic acid (COOH) groups. Preferably, the halogenated hydrocarbons obtained according to the process of the present invention correspond to the general formula $C_nH_{(2n+2)-p}Cl_p$ in which n is an integer and has the values 3 or 4, and p is an integer which has the values 3 to 7. Examples of compounds obtained according to the process of the present invention are 1,1,1,3,3-pentachloropropane, 1,1,1,3,3-pentachlorobutane, 1,1,1,3-tetrachloropropane, 1,1,3,3-tetrachlorobutane, 1,1,1,3,3,3-hexachloropropane and 1,1-dichloro-2-trichloromethylpropane. Among these compounds, 1,1,1,3, 3-pentachloropropane, 1,1,1,3,3-pentachlorobutane and 1,1-dichloro-2-trichlorom ethylpropane are preferred. The process according to the invention applies in particular to the manufacture of 1,1,1,3,3-pentachlorobutane starting with carbon tetrachloride and 2-chloro-1-propene, to the manufacture of 1,1,1,3,3-pentachloropropane starting with carbon tetrachloride and vinyl chloride, and to the manufacture of 1,1,1,3,3,-hexachloropropane starting with carbon tetrachloride and vinylidene chloride.

The molar ratio between the haloalkane and the olefin used can vary within a wide range. This ratio is generally greater than or equal to 0.1. Advantageously, this ratio is greater than or equal to 0.5. In a preferred manner, it is greater than or equal to 1. Generally, this ratio is less than or equal to 15. Advantageously, this ratio is less than or equal to 10. In a preferred manner, this ratio is less than or equal to 5, or even 3.

The catalyst used in the present invention preferably comprises at least one copper compound. Advantageously, this is a copper(II) compound. In a particularly preferred manner, this copper(II) compound is chosen from copper(II) chloride, copper(II) hydroxy chloride, copper(II) acetate, copper(II) acetylacetonate and copper(II) hexafluoroacetylacetonate and mixtures thereof. Excellent results have been obtained with copper(II) chloride, copper(II) acetylacetonate and copper(II) hexafluoroacetylacetonate.

The molar ratio between the catalyst and the olefin is usually greater than or equal to 0.0001. Advantageously, it is greater than or equal to 0.001. Preferably, it is greater than or equal to 0.005. The molar ratio between the Cu(II) compound and the olefin is usually less than or equal to 1. Advantageously, it is less than or equal to 0.5. Preferably, it is less than or equal to 0.1.

The molar ratio between the catalyst and the co-catalyst is chosen such that all the catalyst used is dissolved. This ratio is generally greater than 0.001. Advantageously, this molar ratio is greater than 0.01 and less than 1. A preference is given for molar ratios greater than 0.05 and less than 0.5.

The molar ratio between the co-catalyst and the olefin is generally greater than or equal to 0.01. Preferably, this molar ratio is greater than or equal to 0.05. Advantageously, this molar ratio is greater than or equal to 0.1. However, this molar ratio is usually less than or equal to 2. Preferably, this molar ratio is less than or equal to 1. Advantageously, this molar ratio is less than or equal to 0.5.

It is understood that the above catalyst/olefin and co-catalyst/olefin ratios are expressed, in a non-continous process, relative to the total amount of olefin used, and, in a continuous process, relative to the stationary amount of olefin present in the reactor.

Usually, the reaction takes place at a temperature greater than or equal to room temperature. Preferably, the temperature is greater than or equal to 50° C. Advantageously, the temperature is greater than or equal to 70° C. However, the temperature is generally less than or equal to 200° C. Preferably, the temperature is less than or equal to 175° C. Advantageously, the temperature is less than or equal to 150° C. A very special preference is shown for a temperature of less than or equal to 120° C., or even 100° C.

The reaction time in a non-continuous process or the residence time in a continuous process depends on various parameters, such as the reaction temperature, the concentration of reagents and of catalyst in the reaction mixture and their molar ratios. In general, depending on these parameters, the residence time or the reaction time can range from 5 minutes to 10 hours. Advantageously, in a non-continuous process, the reaction time is generally greater than or equal to 15 minutes. However, the reaction time is usually less than or equal to 10 hours, with a preference for reaction times of less than or equal to 5 hours.

The pressure is generally chosen so as to keep the reaction medium in the liquid phase. The pressure used varies depending on the temperature of the reaction medium. It is usually greater than or equal to atmospheric pressure and less than or equal to 10 bar.

The telomerization reaction is usually carried out in the liquid phase. It can be carried out in the presence of a polar solvent such as an alcohol or a nitrile. Among the alcohols which can be used as solvents for the reaction are, in particular, methanol, ethanol, isopropanol and tert-butanol. Among the nitrites which can be used as solvents for the reaction are aliphatic and aromatic nitrites. Among the aliphatic nitrites are, in particular, acetonitrile, propionitrile and adiponitrile. Among the aromatic nitrites are, in particular, benzonitrile and tolunitrile. Propionitrile and adiponitrile are preferred. The amount of solvent used in the reaction is not critical. However, an excessively dilute solution does not favour a high yield or a high degree of conversion. Preferably, the molar ratio of the solvent to the olefin is greater than or equal to 0.05. Advantageously, this ratio is greater than or equal to 0.1. The molar ratio of the solvent to the olefin is generally less than or equal to 30. Advantageously, it is less than or equal to 20. This ratio is preferably greater than or equal to 1 and less than or equal to 15. However, in the process according to the invention the presence of a co-catalyst in an amount sufficient to dissolve the catalyst generally makes it possible to carry out the reaction in the absence of solvent.

In the process according to the invention, a separation step (b) is carried out. The separation technique may be any separation technique allowing to separate organic compounds having different volatilities such as, for example, a distillation or vapor stripping or stripping. Among these techniques a distillation is preferred.

Should it be the case, the distillation is carried out in a manner which is known per se, in one or, preferably, several distillation columns. It is preferably carried out under reduced pressure.

Preferably, the process according to the invention comprises also a step (c) in which all or some of the fraction containing the catalyst and the cocatalyst are returned into step (a), optionally after additional purification. Other fractions obtained in step (b), notably, should it be the case, a fraction containing the reagents not consumed may also be returned into step (a), optionally after additional purification. In the event of a reduction in the degree of conversion of the olefin, the addition of a supply of fresh co-catalyst and possibly of fresh catalyst makes it possible to regain the initial degree of conversion. The consumption of catalyst and co-catalyst can thus be limited very considerably, as can the amount of waste to be removed.

One of the main advantages of the process according to the invention is that the catalyst remains in dissolved form throughout the separation step (b), which avoids a complicated manipulation of solid compounds. Another advantage of the process is that it makes it possible to obtain the desired chlorinated hydrocarbons with a very high production efficiency and in a very high yield.

The halogenated hydrocarbons obtained according to the process of the invention are precursors of the corresponding fluoro analogues, which can be readily obtained by treatment with hydrogen fluoride in the presence of a catalyst such as an antimony salt, a titanium salt, a tantalum salt, a tin salt or a chromium derivative.

The example below illustrates the invention in a non-limiting manner.

EXAMPLE 1,1,1,3,3-Pentachlorobutane was prepared starting with 2-chloro-1-propene (2-CPe) and carbon tetrachloride, by reaction between these reagents in the presence of copper(II) acetylacetonate and Primene® JM-T amine. To do this, the 2-CPe, the CCl$_4$, the catalyst and the amine were introduced in a molar ratio of 1/2.2/0.02/0.22 into a 300 ml autoclave whose inner walls were lined with Teflon. The device was then closed hermetically, placed in a vertical oven and the temperature was increased gradually and maintained at 90° C. for 1.5 hours. Stirring was provided by a magnetic bar placed at the bottom of the autoclave. At the end of the reaction, the autoclave was allowed to cool and a sample of liquid was taken by syringe and assayed by means of a chromatographic method. The conversion of the 2-CPe was 99%.

The mixture of the reaction products was then subjected to distillation. The excess CCl$_4$ was first removed by distillation, after which the 1,1,1,3,3-pentachlorobutane was removed by distillation under reduced pressure. The solution remaining in the boiling vessel of the column, consisting essentially of the catalyst dissolved in the co-catalyst, was transferred into the telomerization reactor, along with the CCl$_4$ distilled off. 2-Chloro-1-propene and carbon tetrachloride were added thereto in an amount such that the molar ratio between the 2-CPe, the CCl$_4$, the catalyst and the amine was again 1/1.2/0.02/0.22, and the reaction step was then repeated. After reaction for 1.5 hours at 90° C., the degree of conversion of the 2-chloro-1-propene was 92%.

What is claimed is:

1. A process for preparing a halogenated hydrocarbon, comprising the following steps:
    (a) a reaction step between a haloalkane and an olefin in the presence of a catalyst and a co-catalyst under conditions which are suitable for producing the halogenated hydrocarbon, the co-catalyst being chosen from amines which are less volatile than the halogenated hydrocarbon;
    (b) a separation step of the mixture of reaction products from step (a) wherein at least a first fraction comprising the halogenated hydrocarbon and a second fraction comprising the catalyst and the co-catalyst are obtained;
    (c) optionally a recycling step of at least a part of the second fraction into step (a).

2. Process according to claim 1, in which the co-catalyst is an aliphatic amine comprising from 8 to 25 carbon atoms.

3. Process according to claim 1, in which the co-catalyst is chosen from nonylamine, decylamine, undecylamine and dodecylamine.

4. Process according to claim 1, in which the co-catalyst is a tert-alkyl amine corresponding to the general formula (I)

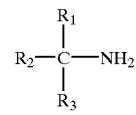

in which R$_1$, R$_2$ and R$_3$ represent C1–C8 alkyl groups and the total carbons of R$_1$, R$_2$, and R$_3$ is from 8 to 25 carbon atoms.

5. Process according to claim 1, in which the catalyst comprises at least one copper compound.

6. Process according to claim 1, in which step (b) is a distillation step.

7. Process according to claim 1, in which in step (b) in addition, a third fraction comprising not consumed reagents is obtained and at least a part of the second fraction and/or of the third fraction is returned to step (a).

8. Process according to claim 1, in which the olefin is a halogenated olefin.

9. Process according to claim 1, applied to the manufacture of 1,1,1,3,3-pentachloro-propane or 1,1,1,3,3-pentachlorobutane.

10. A process for the synthesis of a fluorinated hydrocarbon comprising subjecting a halogenated hydrocarbon obtained by the process as claimed in claim 1, to a treatment with a hydrogen fluoride.

11. The process as claimed in claim 10, wherein said treatment with hydrogen fluoride is carried out in the presence of a catalyst.

12. The process as claimed in claim 11, wherein the catalyst is antimony salt, titanium salt, tantalum salt or tin salt.

13. The process as claimed in claim 2, wherein the catalyst comprises at least one copper compound, the co-catalyst is nonylamine, decylamine, undecylamine or a dodecylamine in which step b) is a distillation step.

14. The process as claimed in claim 13, wherein the olefin is a halogenated olefin.

15. A process for preparing a halogenated hydrocarbon, comprising the following steps:
   (a) a reaction step between a haloalkane and an olefin in the presence of a catalyst and a co-catalyst under conditions which are suitable for producing the halogenated hydrocarbon, the co-catalyst being chosen from amines which are less volatile than the halogenated hydrocarbon;
   (b) a separation step of the mixture of reaction products from step (a) wherein at least a first fraction comprising the halogenated hydrocarbon and a second fraction comprising the catalyst and the co-catalyst are obtained; and
   (c) a recycling step of at least a part of the second fraction into step (a).

16. The process as claimed in claim 1, wherein the amine is an aliphatic amine comprising from 10 to 22 carbon atoms.

17. A process for preparing a halogenated hydrocarbon, comprising the following steps:
   (a) a reaction step between a haloalkane and an olefin in the presence of a catalyst and a co-catalyst under conditions which are suitable for producing the halogenated hydrocarbon, the co-catalyst being chosen from amines which are less volatile than the halogenated hydrocarbon and contain from 8 to 25 carbon atoms;
   (b) a separation step of the mixture of reaction products from step (a) wherein at least a first fraction comprising the halogenated hydrocarbon and a second fraction comprising the catalyst and the co-catalyst are obtained;
   (c) optionally a recycling step of at least a part of the second fraction into step (a).

* * * * *